(12) United States Patent
Goumas et al.

(10) Patent No.: US 12,064,366 B2
(45) Date of Patent: Aug. 20, 2024

(54) THERAPY BOOT WITH POCKETS FOR ICE PACK AND COMPRESSION BLADDER

(71) Applicant: G Force Braces, LLC, Manchester, NH (US)

(72) Inventors: Douglas M. Goumas, Bedford, NH (US); David Scott Westbrook, Nevada, TX (US); Michael N. Bordieri, Jr., Katonah, NY (US); Danielle N. Calvello, Katonah, NY (US)

(73) Assignee: G Force Braces, LLC, Manchester, NH (US)

( * ) Notice: Subject to any disclaimer, the term of this patent is extended or adjusted under 35 U.S.C. 154(b) by 366 days.

(21) Appl. No.: 17/653,297

(22) Filed: Mar. 3, 2022

(65) Prior Publication Data

US 2022/0287864 A1 Sep. 15, 2022

Related U.S. Application Data

(60) Provisional application No. 63/200,504, filed on Mar. 11, 2021.

(51) Int. Cl.
*A61F 5/01* (2006.01)
*A61F 7/00* (2006.01)
*A61F 7/02* (2006.01)

(52) U.S. Cl.
CPC .............. *A61F 5/0111* (2013.01); *A61F 7/02* (2013.01); *A61F 5/0195* (2013.01);
(Continued)

(58) Field of Classification Search
CPC .......... A61F 5/01; A61F 5/012; A61F 5/0102; A61F 5/0104; A61F 5/0111; A61F 5/0127; A61F 5/0195; A61F 2005/0197; A61F 2007/0091; A61F 2007/0203; A61F 2007/0215; A61F 2007/0219; A61F 2007/0225; A61F 2007/0233; A61F 2007/0238

See application file for complete search history.

(56) References Cited

U.S. PATENT DOCUMENTS 2,774,152 A * 12/1956 Alber ................... A43B 5/0407
128/DIG. 20
3,548,819 A 12/1970 Davis et al.
(Continued)

*Primary Examiner* — Alireza Nia
*Assistant Examiner* — Andrew Jun-Wai Mok
(74) *Attorney, Agent, or Firm* — Lipsitz & McAllister, LLC

(57) ABSTRACT

The present invention comprises a therapy boot for treatment of the ankle or lower leg. The therapy boot comprises a hard outer shell having an open anterior portion, a base portion, a posterior portion, two oppositely disposed side portions, and a pocket with an opening provided in each of the side portions. The therapy boot also comprises an air bladder comprising two inflatable chambers, a corresponding one of the two inflatable chambers being disposed on an inside of each of the side portions. Respective gel packs are also provided which are adapted to be inserted into one of the respective openings of the pockets in between the air bladder and at least one of the lower leg or the ankle. The gel packs are pressed against at least one of the lower leg and the ankle by the corresponding inflatable chamber of the air bladder.

19 Claims, 14 Drawing Sheets

(52) U.S. Cl.
CPC ............. *A61F 2007/0043* (2013.01); *A61F 2007/0044* (2013.01); *A61F 2007/0091* (2013.01); *A61F 2007/0219* (2013.01); *A61F 2007/0236* (2013.01); *A61F 2007/0238* (2013.01)

(56) References Cited

U.S. PATENT DOCUMENTS

| | | |
|---|---|---|
| 5,074,285 A | 12/1991 | Wright |
| 5,078,128 A * | 1/1992 | Grim ............... A61F 5/0127 602/23 |
| 5,088,478 A | 2/1992 | Grim |
| 5,407,421 A * | 4/1995 | Goldsmith ............. A61F 7/02 602/5 |
| 5,817,041 A * | 10/1998 | Bader ............... A61F 5/0111 128/882 |
| 2007/0006359 A1* | 1/2007 | Godfrey ........... A41D 13/0058 2/69 |
| 2007/0100264 A1 | 5/2007 | Hanson |
| 2008/0195012 A1* | 8/2008 | Miros ............... A61F 7/02 607/114 |
| 2012/0023782 A1* | 2/2012 | Zaragosa ............ A43B 7/02 36/106 |
| 2013/0072838 A1 | 3/2013 | Fischer et al. |
| 2013/0331753 A1* | 12/2013 | Farrow ............... A61F 5/012 602/16 |
| 2019/0060129 A1 | 2/2019 | Lu |

\* cited by examiner

THERAPY BOOT WITH POCKETS FOR ICE PACK AND COMPRESSION BLADDER

This application claims the benefit of U.S. provisional patent application No. 63/200,504 filed on Mar. 11, 2021, which is incorporated herein and made a part hereof by reference.

BACKGROUND OF THE INVENTION

The present invention relates to the field of therapy boots, in particular those used for recovery from injury or surgery. More specifically, the present invention relates to a therapy boot with pockets for accepting gel packs and which provides targeted compression and cold therapy to the ankle and/or lower leg in a simple manner.

Boots or sleeves for use in recovery from ankle or lower leg injuries or surgery are known, including boots or sleeves that include or accommodate the application of cold or heat elements. Such boots or sleeves are also known to provide compression features as well.

However, such prior art boots or sleeves are cumbersome and difficult to use, and do not apply targeted cold treatment under pressure to the area surrounding the ankle joint (or other targeted areas). For example, U.S. patent publication no. 2007/0100264 to Hanson discloses a treatment boot for ankles and lower legs which includes openings at the top of the boot for ice packs or ice cubes but no pressure mechanism. U.S. Pat. No. 5,074,285 to Wright discloses a garment for the lower leg with a thermal applicator and a pressure applicator, with either wide flaps that run along the length of the garment which must be opened to insert thermal packs, or pockets for ice packs enclosed by a pressure sheath which encloses the entire stocking. Further, U.S. publication no. 2012/0023782 to Zaragosa discloses a thermal treatment boot which includes pockets for ice packs but without a compression mechanism.

It would be advantageous to provide a therapy boot with one or more gel packs for application of heat or cold therapy as well as targeted compression of the gel packs against the patient's leg or ankle. It would be advantageous to provide a simple mechanism for inserting the gel packs that is easy to use as compared to the cumbersome prior art devices.

The present invention provides the foregoing and other advantages.

SUMMARY OF THE INVENTION

The present invention relates to a therapy boot with pockets for accepting gel packs and which provides targeted compression and cold therapy to the ankle and/or lower leg in a simple manner.

In accordance with one example embodiment of the invention, a therapy boot for treatment of the ankle or lower leg is provided. The therapy boot comprises a hard outer shell. The hard outer shell comprises an open anterior portion, a base portion, a posterior portion, two oppositely disposed side portions extending from the base portion and connected to the posterior portion, and a pocket with an opening provided in each of the side portions. A wrap may be fixed to an interior of the hard outer shell and adapted to at least substantially enclose a foot and lower leg of a patient in a fitted position of the therapy boot. The therapy boot also comprises an air bladder comprising two inflatable chambers, a corresponding one of the two inflatable chambers being disposed on an inside of each of the side portions. Gel packs are provided, each of which is adapted to be inserted through a corresponding one of the openings into one of the pockets in between the air bladder and at least one of the lower leg or the ankle to provide heat or cold to at least one of the lower leg and the ankle. Upon pressurization of the air bladder, the gel packs are pressed against at least one of the lower leg and the ankle by the corresponding inflatable chamber of the air bladder.

The hard outer shell may further comprise respective extensions which extend from the corresponding side portions in an anterior direction to at least partially enclose a foot of a patient in the fitted position, a bottom section of each of the extensions being connected to corresponding sides of the base portion.

The hard outer shell may comprise at least one of a molded plastic material, a synthetic material, a fiberglass material, a composite material, a carbon fiber material, or the like. The hard outer shell may be sufficiently rigid to prevent flexion of the ankle and to immobilize the lower leg.

The wrap may be contoured to conform to the interior of the hard outer shell. The wrap may comprise an anterior opening corresponding to the open anterior portion of the hard outer shell and slits corresponding to the openings in the pockets. The anterior opening of the wrap may be formed by open ends of the wrap which when in a closed position overlap one another to encase at least the lower leg and a portion of a foot of the patient. The wrap may further comprise closing means for securing the open ends of the wrap together. The closing means may comprise one of hook and loop fasteners or straps. Alternatively, in an embodiment where the open ends of the wrap do not overlap, the anterior opening of the wrap may be closed via one of a zipper, snap fasteners, laces, straps, or the like.

The air bladder may be removably fixed to the wrap. Alternatively, the air bladder may be disposed within layers of the wrap.

The air bladder may further comprise a bridge section connecting the two inflatable chambers. Each of the corresponding one of the two inflatable chambers may be disposed on an inside of each of the side portions adjacent the ankle or the lower leg of the patient.

The two inflatable chambers may each comprise one of rectangularly shaped chambers vertically arranged in the side portions or contoured chambers corresponding to a shape of the ankle. The bridge section may comprise a thinner chamber horizontally arranged in the posterior portion.

At each of the side portions, one of the gel packs may be positioned so as to abut a corresponding one of the two inflatable chambers of the air bladder.

Each pocket may be configured to accommodate the wrap and the corresponding one of the two inflatable chambers of the air bladder such that the gel packs are insertable into the openings of the pockets and through slits of the wrap such that the gel packs abut against the ankle or the lower leg of the patient when the therapy boot is in the fitted position, prior to the pressurization of the air bladder.

The air bladder may comprise a connection mechanism for connecting to an air pump for pressurizing the air bladder. The air pump may be one of an external air pump or an air pump that is integrated into the therapy boot.

The therapy boot may further comprise one of caps or covers for each of the openings of the pockets. The caps or covers may comprise one of removable covers separate from the therapy boot or covers fixed in a hinged manner to a portion of the therapy boot.

The wrap may comprise at least one of a neoprene material, a foam material, a fabric material, a foam fabric laminate material, or the like.

The therapy boot may further comprise a front cover adapted to close off the open anterior portion of the hard shell.

The therapy boot may further comprise one or more additional pockets for accommodating additional gel packs and additional inflatable chambers of the air bladder. The one or more additional pockets may be correspondingly arranged in one or more of upper sections of the side portions above an ankle region, an upper section of the posterior portion adjacent a calf region, and a lower section of the posterior portion adjacent an ankle region, or other regions designed to treat specific injuries or surgical wounds.

BRIEF DESCRIPTION OF THE DRAWINGS

The present invention will hereinafter be described in conjunction with the appended drawing figures, wherein like reference numerals denote like elements, and.

DETAILED DESCRIPTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The present invention relates to a therapy boot which provides targeted compression and cold therapy to the ankle and/or lower leg in a simple manner.

FIGS. 1-15 show various views and embodiments of a therapy boot 10 in accordance with the present invention.

Figure 8:
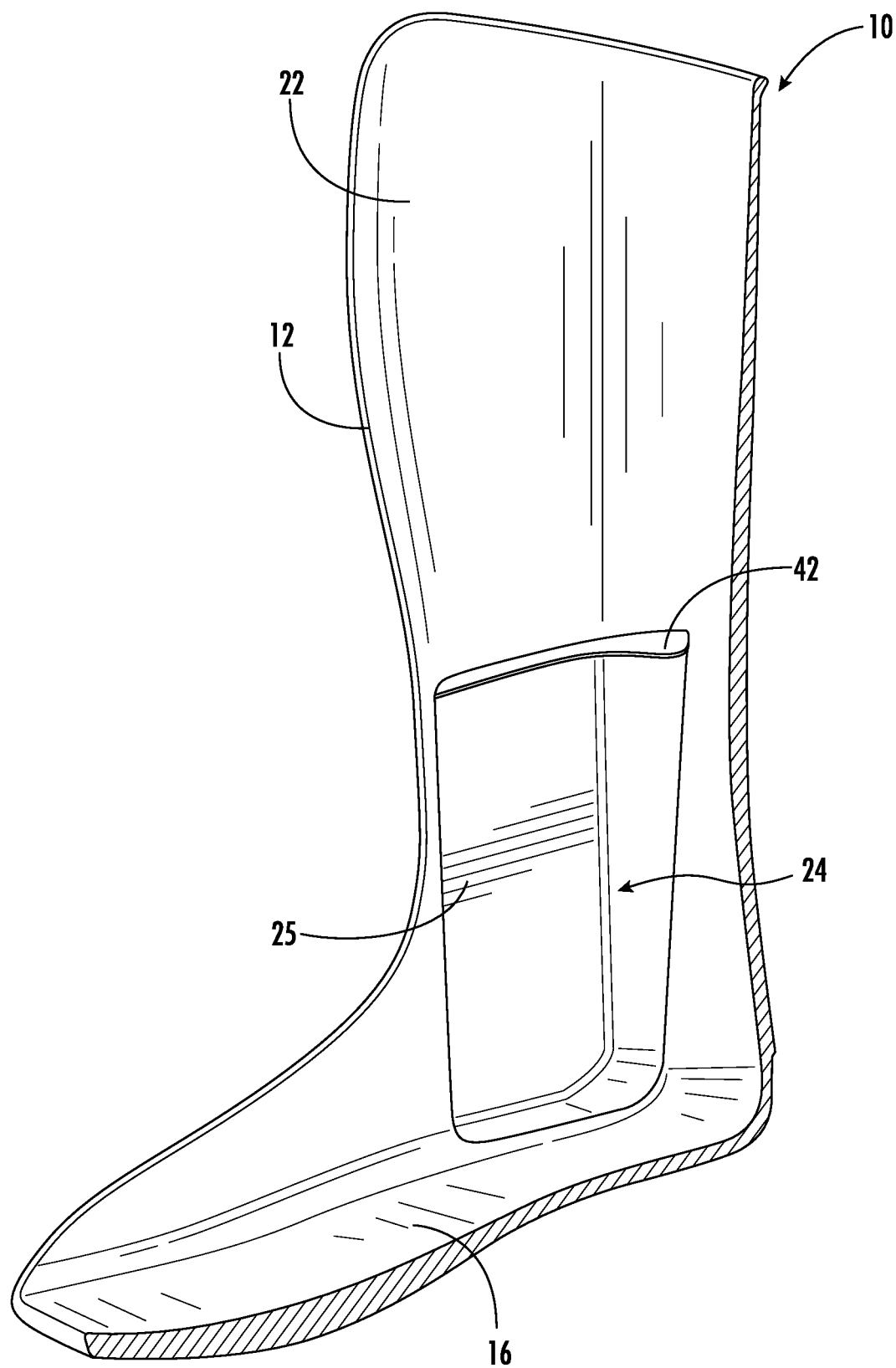
FIG. 8 shows a cutaway view of an example embodiment of a therapy boot in accordance with the present invention.

The therapy boot 10 may comprise a hard outer shell 12 with an open anterior portion 14 enabling the shell to be slipped on from behind. The shell 12 comprises a base portion 16 for supporting the foot of a patient, a posterior portion 18 and two oppositely disposed side portions, a first side portion 20 and a second side portion 22. The base portion 16 may extend to cover the entire sole of the patient's foot. The side portions 20, 22 may extend from the base portion 16 up to at least the top of the calf of the patient. A pocket 24 with an opening 42 is provided in both the first side portion 20 and in the second side portion 22. FIG. 8 shows a cross-section of the shell 12, illustrating the inside 25 of the pocket 24.

The side portions 20, 22 may also include respective extensions 21, 23 which extend from the corresponding side portions 20, 22 in an anterior direction to at least partially enclose corresponding sides of the patient's foot in a fitted position of the boot 10. A bottom section of each of the side portions 20, 22 may be connected to corresponding sides of the base portion 16.

The shell 12 may comprise at least one of a molded plastic material, a synthetic material, a fiberglass material, a composite material, a carbon fiber material, combinations thereof, or the like. The shell 12 may be sufficiently rigid to prevent flexion of the ankle joint and immobilize the lower leg and ankle of the patient.

Figure 9:
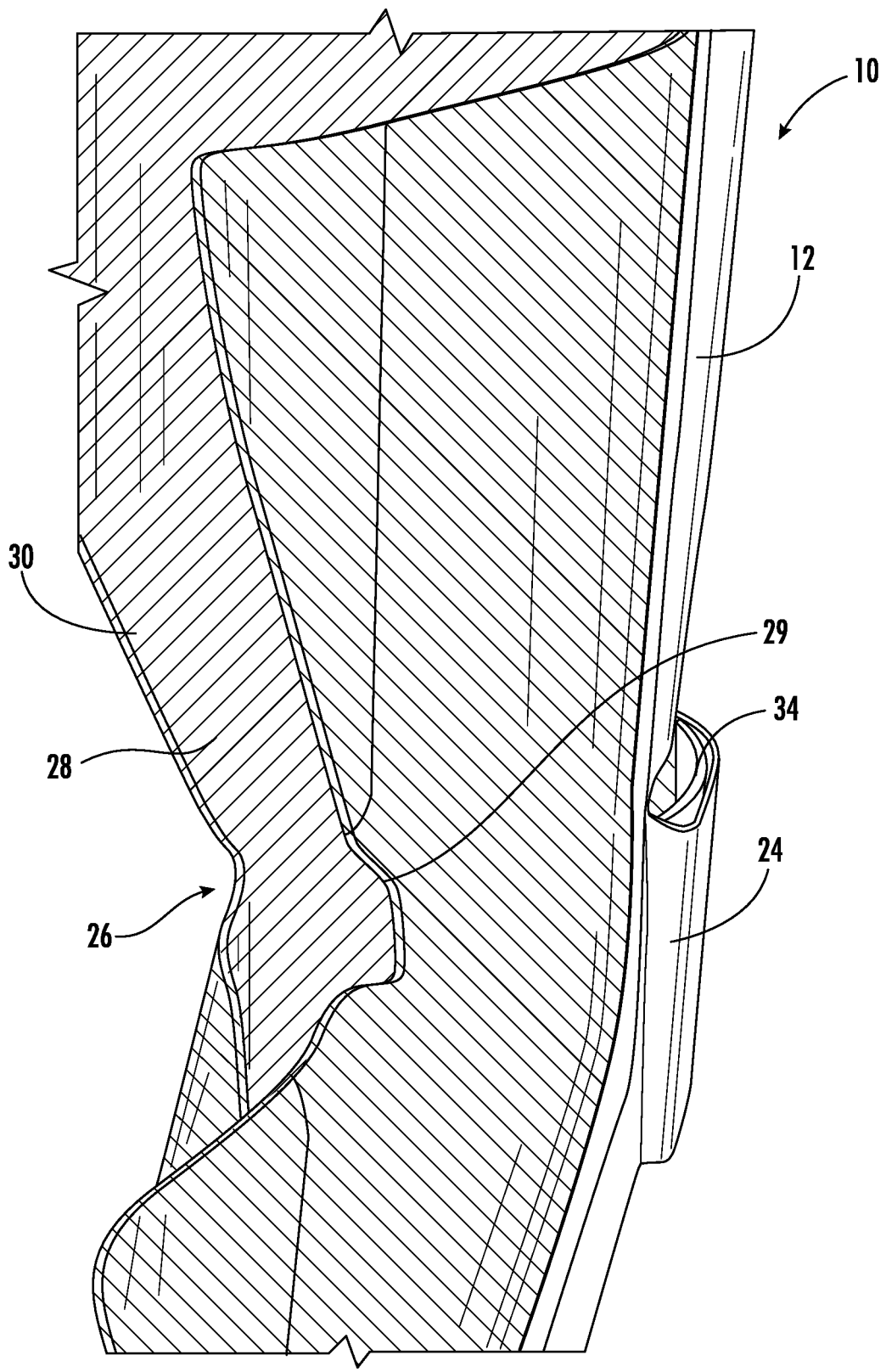
FIGS. 9 and 10 show partial cutaway views of an example embodiment of a therapy boot with the wrap in accordance with the present invention.
Figure 10:
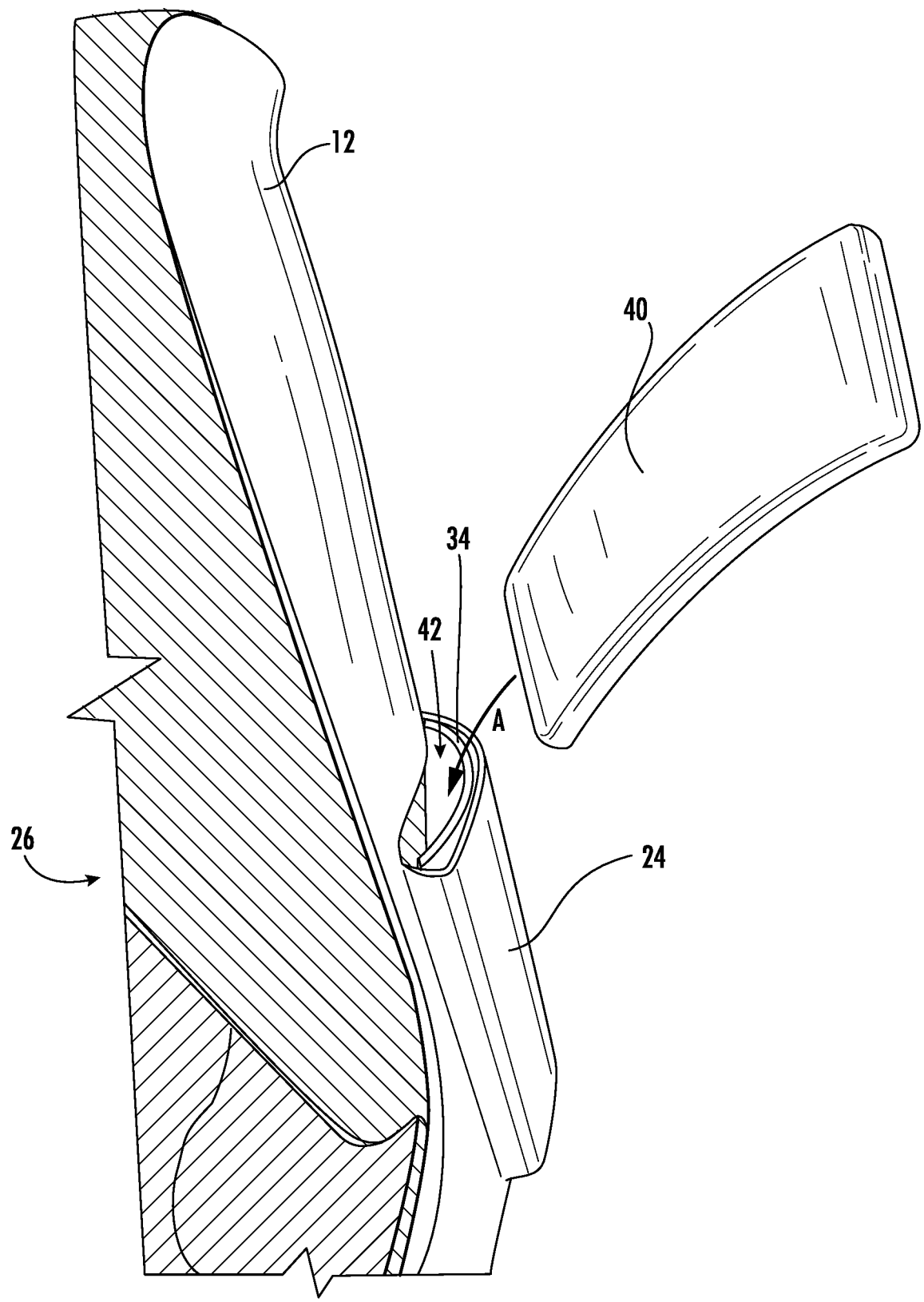
Figure 11:
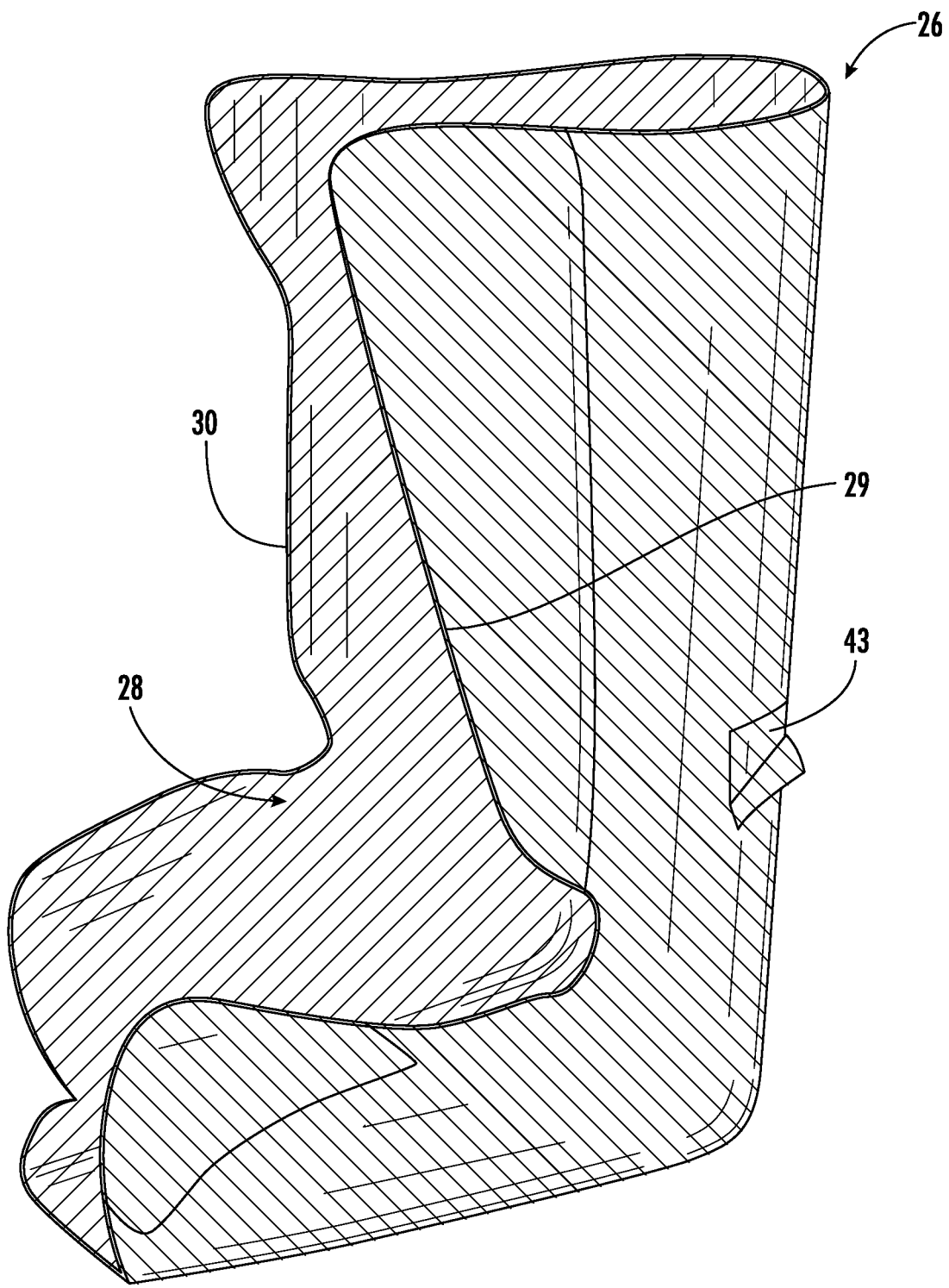
FIG. 11 shows an example embodiment of the wrap used with a therapy boot in accordance with the present invention.

The therapy boot 10 may also comprise a wrap 26 fixed to an interior of the hard outer shell 12 as shown in FIGS. 9 and 10. FIG. 11 shows an example embodiment of a wrap 26 in accordance with the present invention. The wrap 26 may be contoured to fit within the shell 12 and generally shaped in accordance with the shape of the interior of the shell 12. The wrap 26 may be fixed to the inside of the shell 12 via a hook and loop type fastener such as Velcro. The fabric of the wrap 26 may comprise the loop, with a corresponding hook type fabric fixed to the shell 12 to interact with the loops of the wrap 26. The wrap 26 has an anterior opening 28 corresponding to the shell opening 14. The wrap 26 may also be provided with slits 43 corresponding to the openings 42 of the pocket 24. Once the boot 10 is fitted to the lower leg of the patient, the wrap 26 may be closed to completely encase the lower leg and foot of the patient. The wrap 26 may comprise one or more of a foam material, a fabric material, a foam fabric laminate material, a neoprene material, or the like. The wrap 26 may conform to the entire interior of the shell 12.

The anterior opening 28 of the wrap 26 may be formed by open ends 29, 30 which can be brought together into a closed position so that the wrap can completely encase the foot and lower leg of the patient in a closed position. For example, the wrap 26 may comprise ends 29, 30 which may overlap each other when in a closed position and be connected to each other via Velcro or other similar fastening means. Alternatively, the open ends 29, 30 of the wrap may meet each other without overlapping and may be closed using a zipper, snap fasteners, laces, straps, or other types of fastener.

Figure 12:
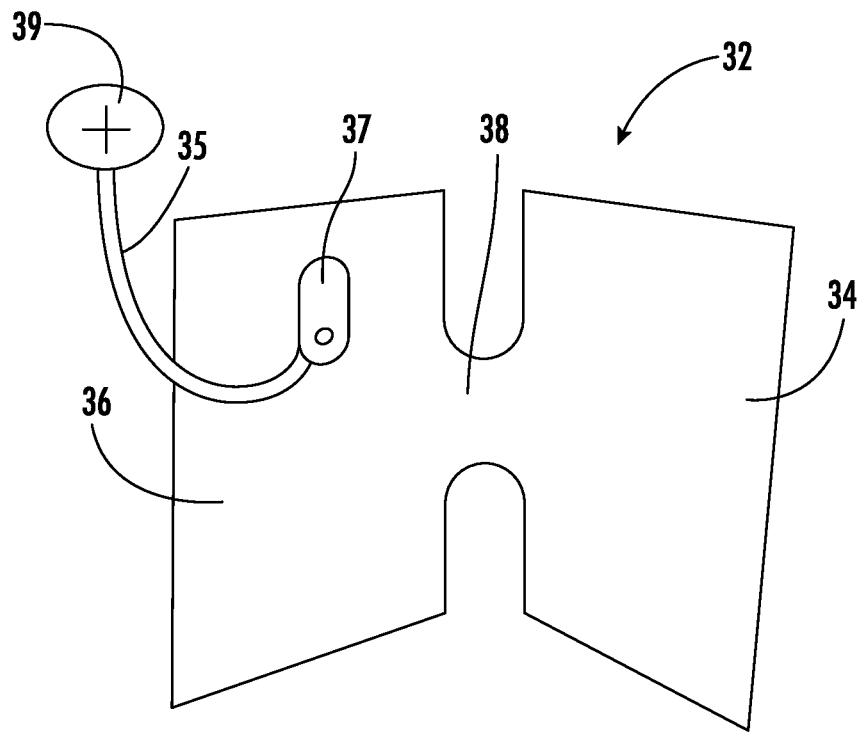
FIG. 12 shows an example embodiment of an air bladder used with a therapy boot in accordance with the present invention.

The therapy boot 10 may also comprise an air bladder 32. An example embodiment of an air bladder 32 is shown in FIG. 12. The air bladder 32 may be sewn onto the wrap 26 or affixed thereto in a removable manner, e.g., using Velcro type fasteners, snap fasteners, or other similar fastening means. Alternatively, the air bladder 32 may be disposed within an interior of the wrap 26, for example between layers of the wrap 26. The air bladder 32 may comprise two inflatable chambers 34, 36 connected by a bridge section 38 that allows air to flow between the chambers 34, 36. Whether fixed to the wrap 26 or integral to the wrap 26, the corresponding chambers 34, 36 of air bladder 32 will be positioned adjacent either side of the ankle of the patient within the boot 10 on an inside of each of the side portions 20, 22 of the shell 12. Each chamber 34, 36 is designed to abut one of the gel packs 40 and press the gel pack 40 against a corresponding side of the ankle of the patient, with the bridge section 38 wrapping around the back of the ankle and connecting the two chambers 34, 36. The chambers 34, 36 may be elongated chambers designed to be positioned in a vertical arrangement in the wrap 26, with the bridge section 38 comprising a thinner horizontal section connecting the two vertically arranged chambers 34, 36. For example, the chambers 34, 36 may be rectangular or substantially rectangular. Alternatively, the chambers 34, 36 may each be contoured (e.g., with a thinner top portion flowing into a wider lower portion) to better fit around the ankle joint. The bridge section 38 may connect the chambers 34, 36 at a mid-portion of the chambers 34, 36 (as shown in FIG. 12) or at an upper portion of the chambers 34, 36.

The air bladder 32 may comprise a nozzle 37 or other connection mechanism for connecting the air bladder 32 to an air pump 39 for pressurizing the chambers 34, 36, e.g., via a tube or hose 35. The air pump 39 may be an external air pump or an air pump integrated into the boot 10 (either in the shell 12 or the wrap 26).

Figure 13:
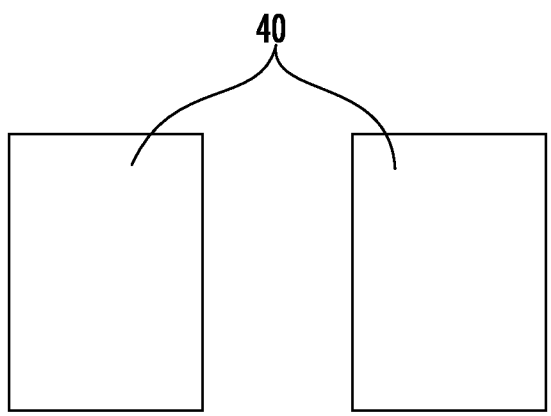
FIG. 13 shows an example embodiment of gel packs used with a therapy boot in accordance with the present invention.

The therapy boot 10 may also comprise at least one gel pack 40 adapted to fit within each pocket 24. FIG. 13 shows an example embodiment of the gel packs 40. The gel pack 40 can be heated or frozen for the application of heat or cold to the ankle area.

The pocket 24 may be molded into the outer shell 12 and provides a gap between the outer shell 12 and the ankle of the patient. The pocket 24 may extend from just above the ankle to the foot of the patient. The pocket 24 has a proximal opening 42 for accepting the gel pack 40. The gel pack 40 may be rectangular or substantially rectangular in shape (as shown in FIG. 13) or may correspond to the shape of the chambers 34, 36 of the air bladder 32. The gel packs 40 may also be contoured to better conform to the shape of the ankle joint.

Figure 14:
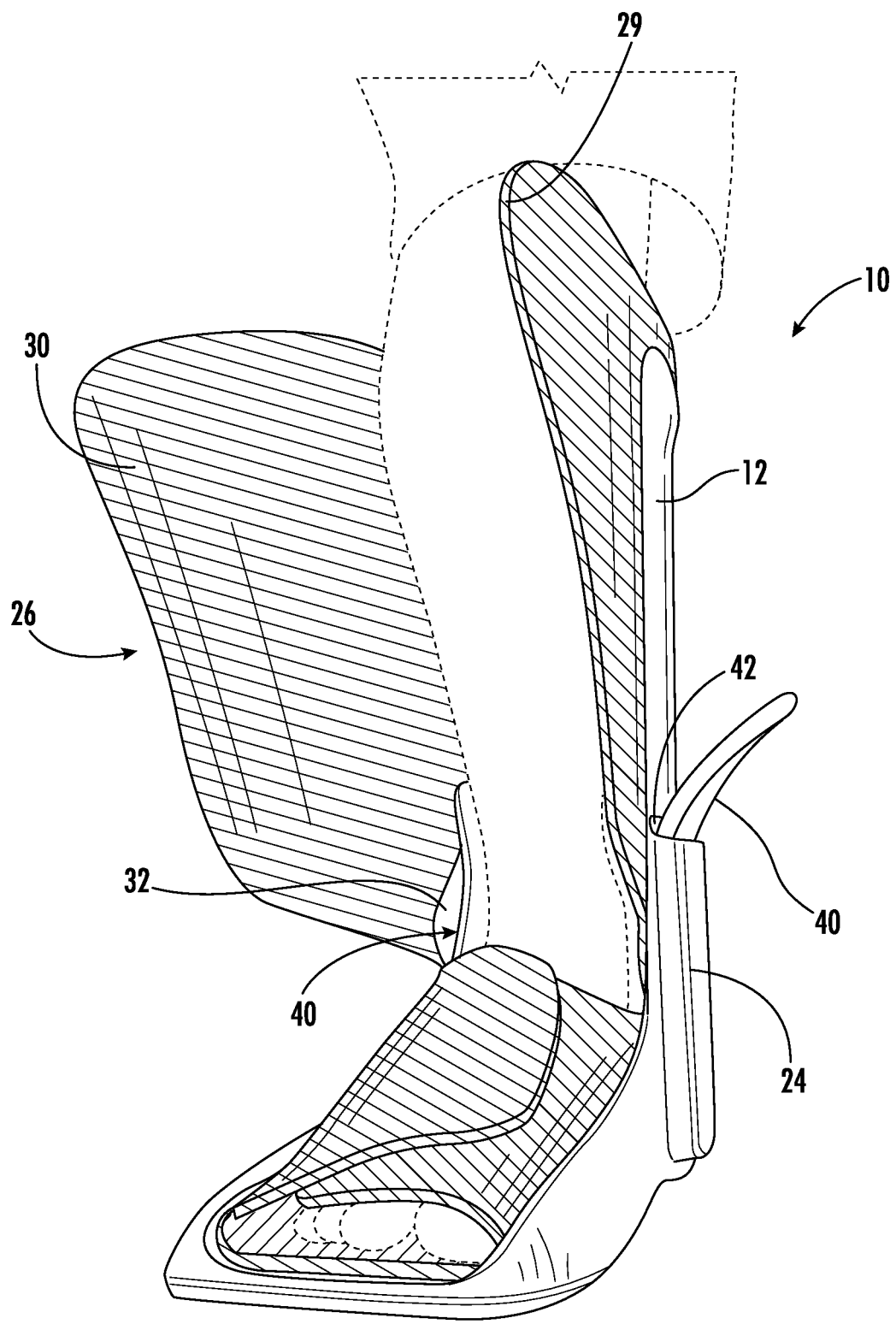
FIG. 14 shows an example embodiment of a therapy boot in accordance with the present invention when fitted to the lower leg of a patient.

The pocket 24 is configured to accommodate the wrap 26 and the corresponding chamber 34 or 36 of the air bladder 32 such that the corresponding chambers 34, 36 are positioned against the inner wall of the pocket 24 with a sufficient gap to allow the gel pack 40 to be inserted through the opening 42 of the pocket 24 and through the slits 43 of the wrap 26 and abut against the ankle or lower leg of the patient when the boot 10 is fitted to the patient. FIG. 9 shows the pocket 24 with the chamber 34 of the air bladder 32 positioned against the inner wall of the pocket 24. As shown in FIGS. 10 and 14, the gel pack 40 can then be inserted through the opening 42 in the shell 12 and through the slit 43 of the wrap, to allow the gel pack 40 to be placed against the skin of the patient's ankle or lower leg. The air bladder 32 can then be inflated using pump 39 so that the inflatable chambers 34, 36 are pressurized, pressing the gel packs 40 against the ankle joint or lower leg of the patient, providing cold (or heat) therapy together with compression targeted to the ankle joint.

Figure 1:
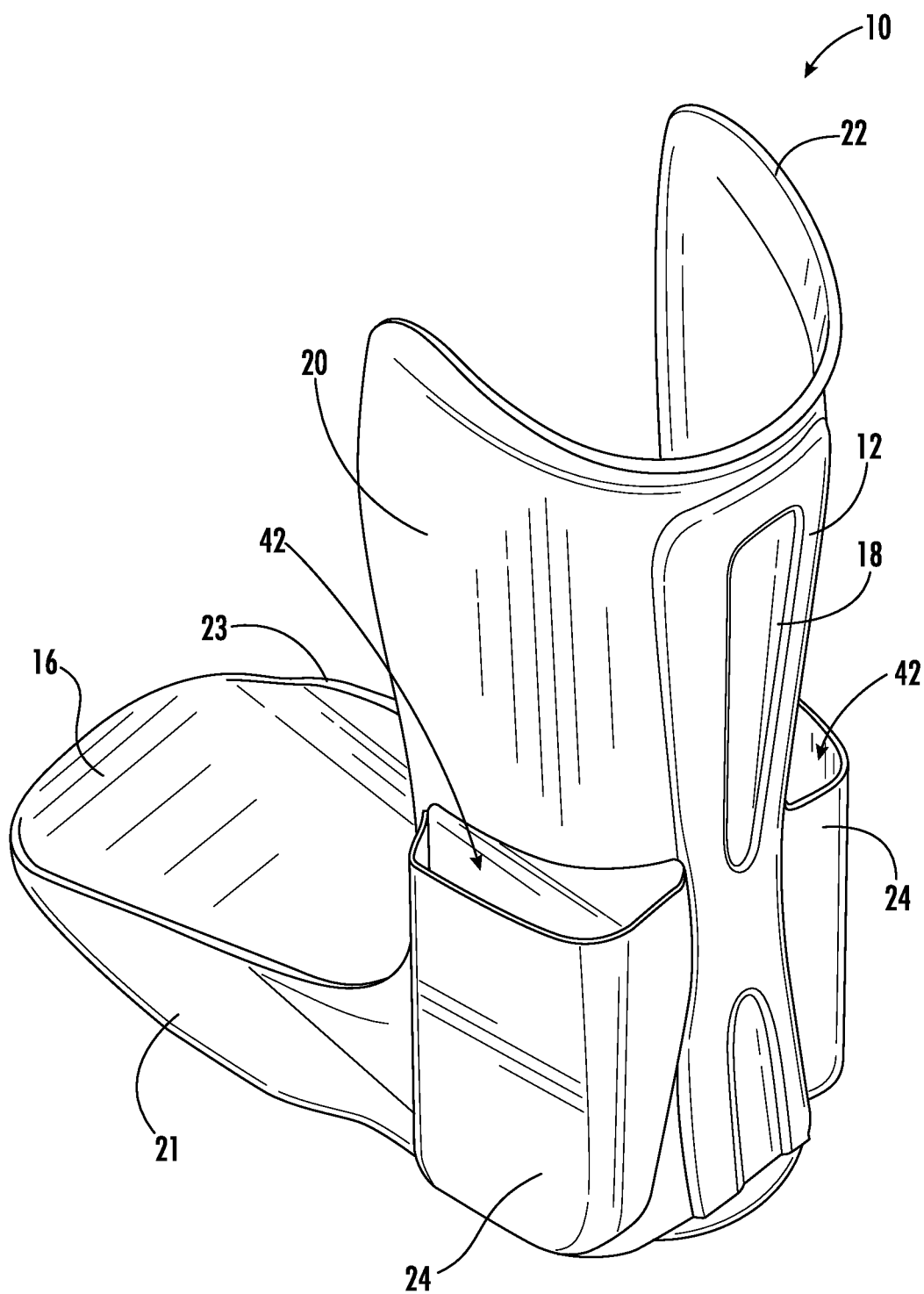
FIG. 1 shows a perspective view of an example embodiment of the therapy boot without the wrap in accordance with the present invention.
Figure 2:
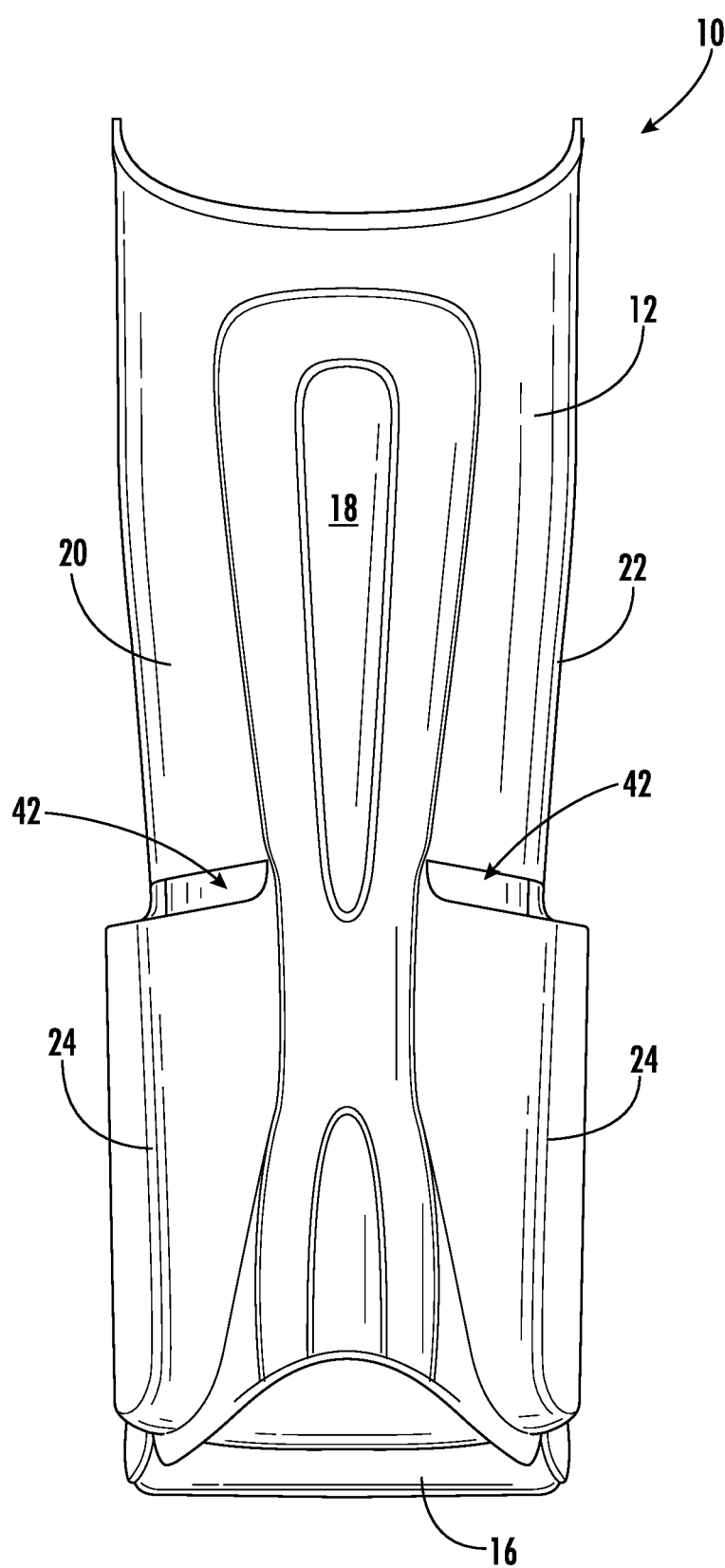
FIG. 2 shows a rear view of the therapy boot of FIG. 1.
Figure 3:
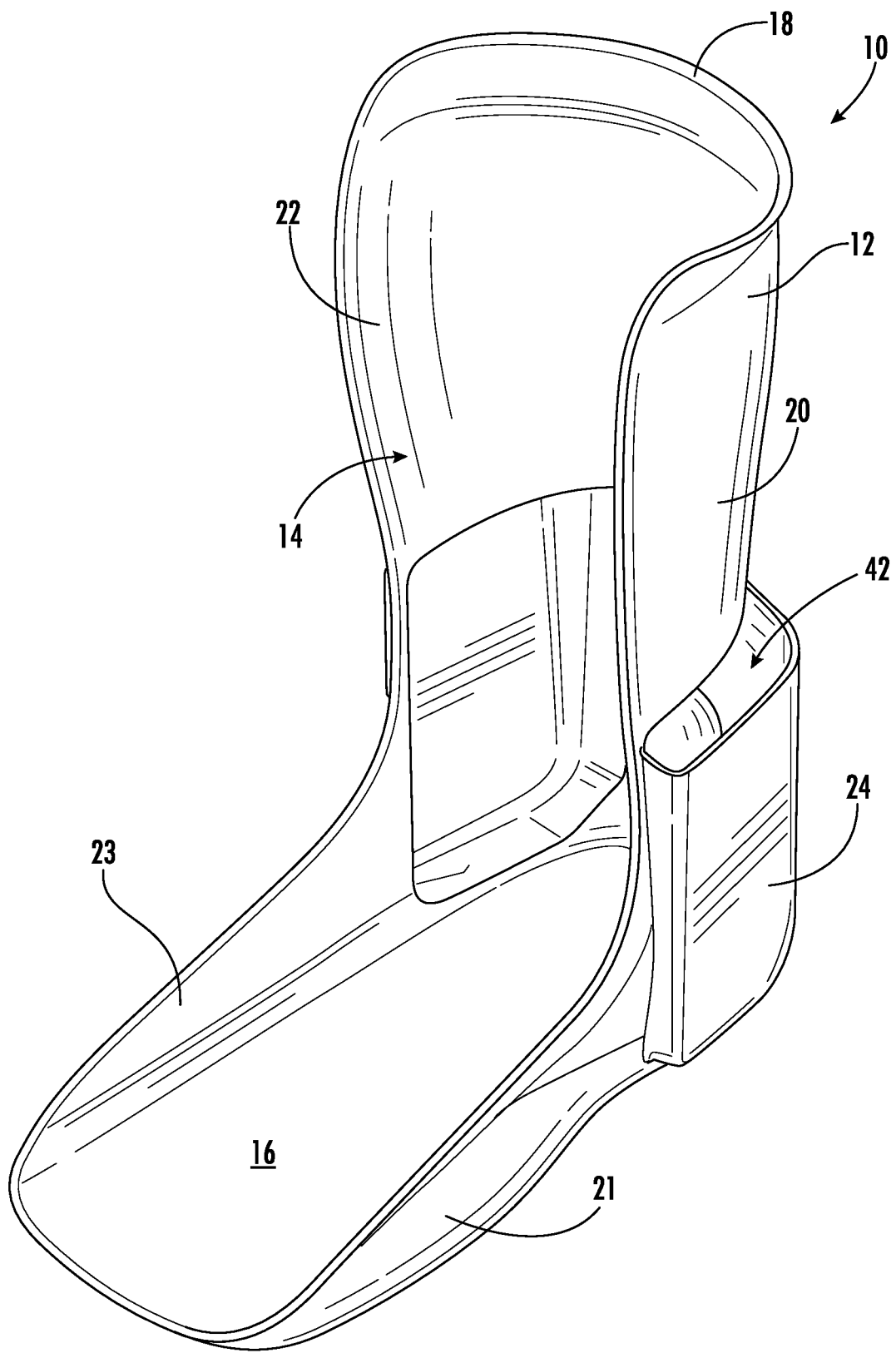
FIGS. 3-7 show further perspective views of example embodiments of therapy boots in accordance with the present invention.
Figure 4:
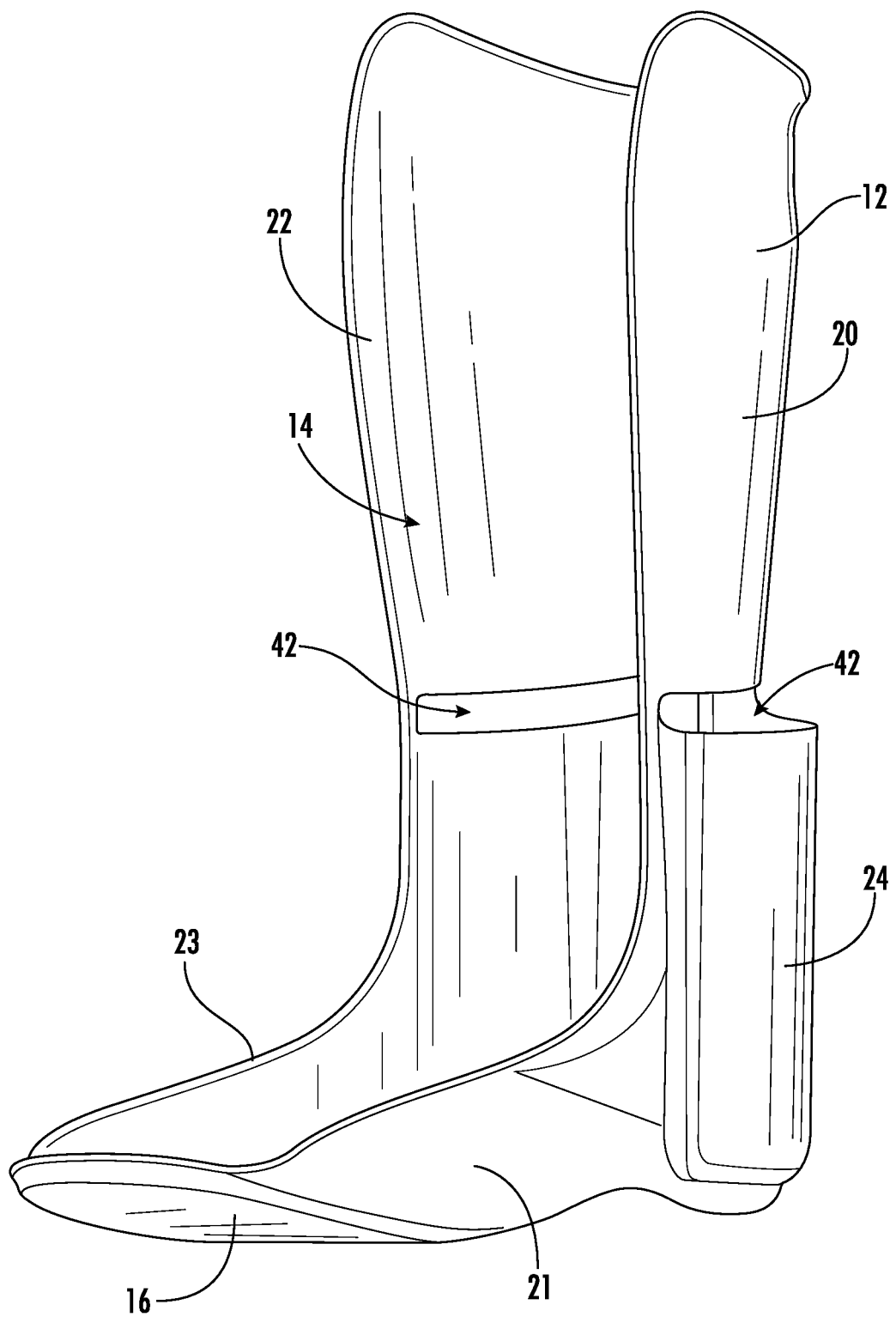
Figure 5:
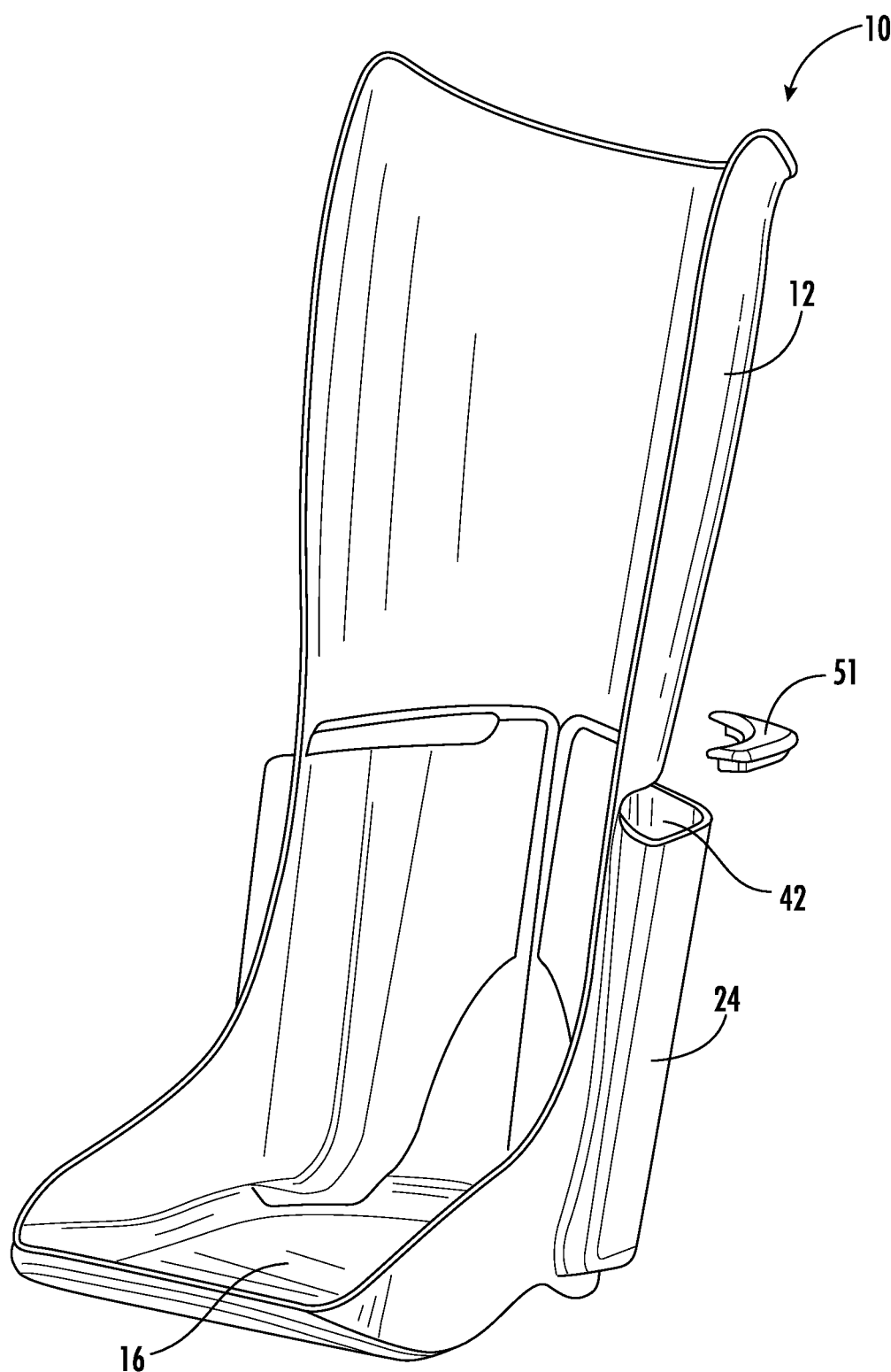
Figure 6:
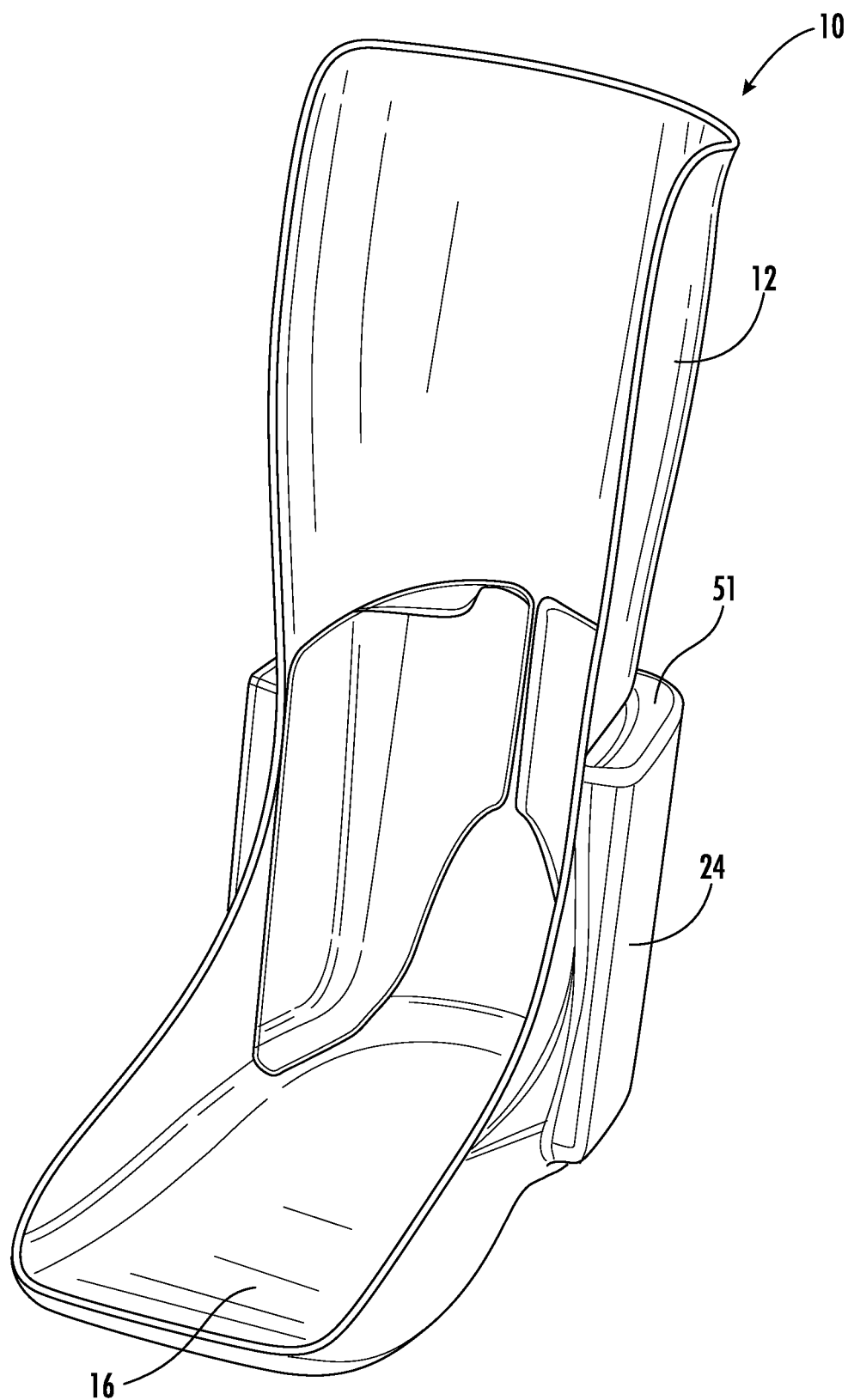

Caps or covers 51 may be provided to close the openings 42 of the pockets 24 to prevent foreign material from entering the pockets 24, as shown in FIGS. 5 and 6. The covers 51 may be made of a rubber or plastic material and be removably secured to the pocket opening 42 via a snap fit or press fit. Alternatively, the covers 51 may be fixed to the outer side of the shell 12 in a hinged manner, e.g., via a flexible plastic strip. Alternatively, the covers may be connected to the gel pack 40, to the air bladder 32, or be separate pieces.

Figure 7:
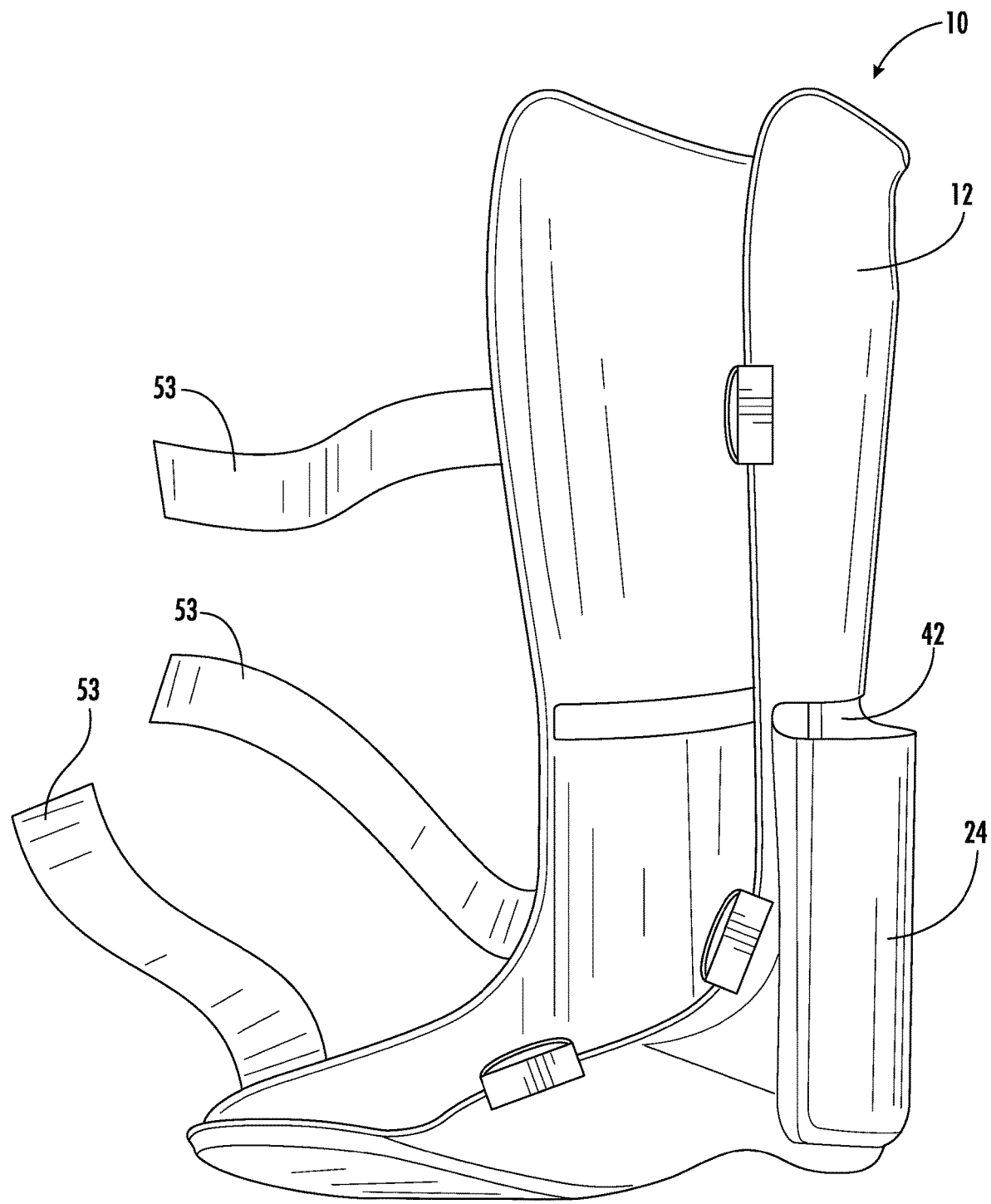
Figure 15:
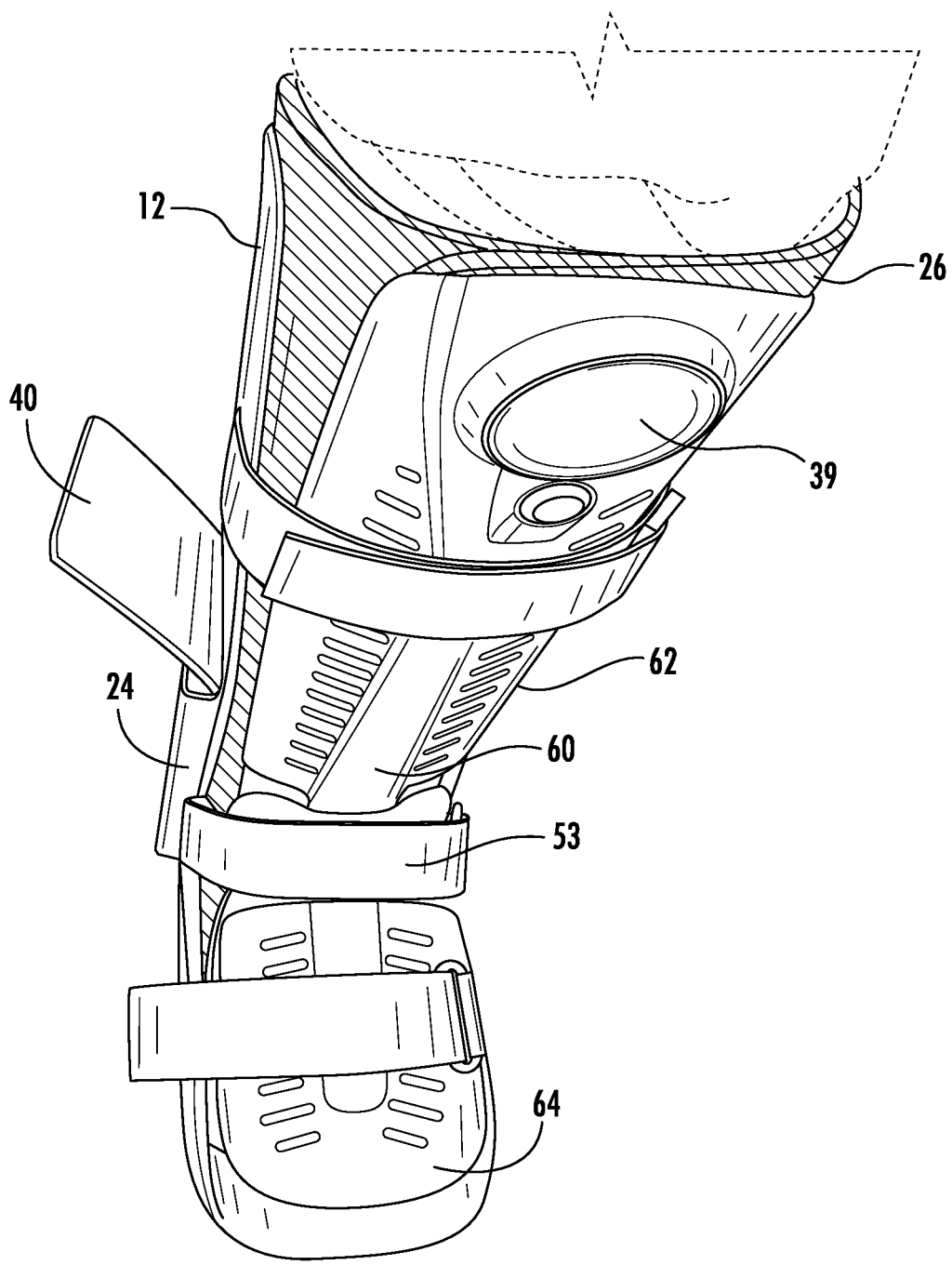
FIG. 15 shows a further example embodiment of a therapy boot in accordance with the present invention when fitted to the lower leg of a patient.

FIGS. 9 and 10 show the boot 10 assembly comprising the outer shell 12, the wrap 26 fixed to the inside of the outer shell 12, and the chamber 34 of the air bladder 32 (fixed to the wrap 26 or integrated into the wrap 26). The boot assembly 10 is slipped on to the lower leg and foot of the patient from behind. FIGS. 14 and 15 show the boot assembly 10 fitted to a patient. The ends 29, 30 of the wrap 26 can then be drawn around the front of the patient's leg and secured together, for example with a hook and loop type fastener such as Velcro. The hook and loop fasteners may be integrated into the ends 29 and 30 of the wrap 26, or the ends 29 and 30 may be fitted with Velcro straps. The entire boot assembly 10 may be secured to the leg using one or more straps 53 attached to the shell 12, as shown in FIG. 7.

As shown in FIG. 15, a front cover 60 may be provided to close off the open anterior portion 14 of the shell 12. The front cover 60 may be made of the same material as the shell 12. The front cover 60 may comprise an upper portion 62 that covers the user's shin and a hinged lower portion 64 that covers the top of the wearer's foot. The front cover 60 may be connected to the shell 12 by straps 53 that secure the boot 10 on the wearer.

FIG. 15 shows an embodiment where the pump 39 is integrated into the upper portion 62. Those skilled in the art will appreciate that the pump 39 may be integrated into other portions of the therapy boot 10. For example, the pump 39 may be integrated into either one of the side portions 20, 22 of the shell 12, the posterior portion 18 of the shell 12, the lower portion 64 of the front cover 62, or the like. The pump 39 may also be integrated into the wrap 26.

The gel pack 40, whether frozen or heated, can then be slipped into the pocket 24 (in the direction of arrow A as shown in FIG. 10) so that it rests against the patient's ankle on one side and against the air bladder 32 (or against the wrap 26 with integral air bladder 32) on the other side. The air bladder 32 can then be inflated using an air pump 39 to pressurize the chambers 34, 36. The chambers 34, 36 apply pressure against the gel pack 40, pressing it against the patient's ankle. When treatment is complete, the air can be released from the air bladder 32. The boot 10 can be removed either before or after the gel pack 40 is removed from the pocket 24. If continuous treatment is required or desired, the gel pack 40 can be removed from the pocket 24 and replaced with a newly frozen or heated gel pack 40.

The therapy boot 10 can also be worn without the gel pack 40 in place to provide stability to the ankle joint between treatments, with or without the air bladder 32 inflated.

The therapy boot 10 may be configured as a walking boot. Further, the boot 10 may be produced in a variety of sizes for men, women, and children. Further, various portions of the top part of the therapy boot 10 may be adapted to be cut to accommodate a patient with a large calf muscle.

It should be appreciated that although the present invention has been described for use in the treatment of the ankle, the present invention can be easily adapted to treat different areas of the lower leg or foot, by providing the pockets, air bladder and gel packs in different locations in the boot 10. For example, one or more additional pockets 42 may be provided for accommodating additional gel packs and additional inflatable chambers of the air bladder 32. The one or more additional pockets 42 may be correspondingly arranged in one or more of upper sections of the side portions 20, 22 above an ankle region, an upper section of the posterior portion 18 adjacent a calf region, and a lower section of the posterior portion 18 adjacent an ankle region, or other regions designed to treat specific injuries or surgical wounds.

It should be further appreciated that the present invention provides advantageous therapy boot for the treatment of injured or surgically repaired ankles.

Although the invention has been described in connection with various illustrated embodiments, numerous modifications and adaptations may be made thereto without departing from the spirit and scope of the invention as set forth in the claims.

What is claimed is:

1. A therapy boot for treatment of an ankle or lower leg, comprising:
    a hard outer shell, comprising an open anterior portion, a base portion, a posterior portion, two oppositely disposed side portions extending from the base portion and connected to the posterior portion, and a pocket with an opening provided in each of the side portions;
    a wrap fixed to an interior of the hard outer shell and adapted to enclose at least a lower leg and a portion of a foot of a patient in a fitted position of the therapy boot;
    an air bladder comprising two inflatable chambers, a corresponding one of the two inflatable chambers being disposed on an inside of each of the side portions; and
    respective gel packs, one of the respective gel packs adapted to be inserted through a corresponding one of the openings into a corresponding one of the pockets in between the air bladder and at least one of the lower leg or the ankle to provide heat or cold to at least one of the lower leg and the ankle;
    wherein:
    upon pressurization of the air bladder, the gel packs are configured to be pressed against at least one of the lower leg and the ankle by the corresponding inflatable chamber of the air bladder; and
    each pocket is configured to accommodate the wrap and the corresponding one of the two inflatable chambers of the air bladder such that the gel packs are insertable into the openings of the pockets and through slits of the wrap such that the gel packs are configured to abut against the ankle or the lower leg of the patient when the therapy boot is in the fitted position, prior to the pressurization of the air bladder.

2. The therapy boot in accordance with claim 1, wherein:
    the wrap is contoured to conform to the interior of the hard outer shell;
    the wrap comprises an anterior opening corresponding to the open anterior portion of the hard outer shell and slits corresponding to the openings in the pockets.

3. The therapy boot in accordance with claim 2, wherein the anterior opening of the wrap is formed by open ends of the wrap which when in a closed position overlap one another to encase at least the lower leg and the portion of the foot of the patient.

4. The therapy boot in accordance with claim 3, wherein the wrap further comprises closing means for securing the open ends of the wrap together, the closing means comprising one of hook and loop fasteners or straps.

5. The therapy boot in accordance with claim 2, wherein the anterior opening of the wrap is closed via one of a zipper, snap fasteners, laces, or straps.

6. The therapy boot in accordance with claim 1, wherein:
    the air bladder further comprises a bridge section connecting the two inflatable chambers; and
    each of the corresponding one of the two inflatable chambers is disposed on an inside of each of the side portions.

7. The therapy boot in accordance with claim 6, wherein:
    the two inflatable chambers each comprise one of rectangularly shaped chambers vertically arranged in the side portions or contoured chambers corresponding to a shape of the ankle; and
    the bridge section comprising a thinner chamber horizontally arranged in the posterior portion.

8. The therapy boot in accordance with claim 1, wherein the air bladder comprises a connection mechanism for connecting to an air pump for pressurizing the air bladder.

9. The therapy boot in accordance with claim 8, wherein the air pump is one of an external air pump or an air pump that is integrated into the therapy boot.

10. The therapy boot in accordance with claim 1, further comprising one of caps or covers for each of the openings of the pockets.

11. The therapy boot in accordance with claim 10, wherein the caps or covers comprise one of removable covers separate from the therapy boot or covers fixed in a hinged manner to a portion of the therapy boot.

12. The therapy boot in accordance with claim 1, wherein the hard outer shell further comprises respective extensions which extend from the corresponding side portions in an anterior direction which are adapted to at least partially enclose the foot of the patient in the fitted position, a bottom section of each of the extensions being connected to corresponding sides of the base portion.

13. The therapy boot in accordance with claim 1, wherein the hard outer shell comprises at least one of a molded plastic material, a synthetic material, a fiberglass material, a composite material, and a carbon fiber material.

14. The therapy boot in accordance with claim 1, wherein the hard outer shell is sufficiently rigid to prevent flexion of the ankle and to immobilize the lower leg.

15. The therapy boot in accordance with claim 1, wherein the air bladder is removably fixed to the wrap.

16. The therapy boot in accordance with claim 1, wherein the air bladder is disposed within layers of the wrap.

17. The therapy boot in accordance with claim 1, wherein, at each of the side portions, one of the gel packs is positioned so as to abut a corresponding one of the two inflatable chambers of the air bladder.

18. The therapy boot in accordance with claim 1, wherein the wrap comprises at least one of a neoprene material, a foam material, a fabric material, and a foam fabric laminate material.

19. The therapy boot in accordance with claim 1, further comprising a front cover adapted to close off the open anterior portion of the hard shell.

* * * * *